United States Patent [19]

Yao et al.

[11] Patent Number: 5,716,623

[45] Date of Patent: Feb. 10, 1998

[54] **ISOLATED *HERPESVIRUS SAIMIRI* PROTEINS THAT BIND MHC CLASS II MOLECULES**

[75] Inventors: Zhengbin Yao; Melanie K. Spriggs, both of Seattle; Mark Alderson; Richard J. Armitage, both of Bainbridge Island, all of Wash.

[73] Assignee: Immunex Corporation, Seattle, Wash.

[21] Appl. No.: 485,549

[22] Filed: Jun. 6, 1995

Related U.S. Application Data

[63] Continuation-in-part of Ser. No. 351,901, Dec. 7, 1994.

[51] Int. Cl.[6] .................... A61K 39/12; A61K 39/00; A61K 39/245; C07K 1/00; C07C 245/00
[52] U.S. Cl. .................... 424/186.1; 424/192.1; 424/229.1; 424/231.1; 530/350; 530/226; 435/693; 435/697
[58] Field of Search .................... 530/350, 826; 435/69.3, 69.7; 424/186.1, 192.1, 229.1, 231.1

[56] References Cited

FOREIGN PATENT DOCUMENTS

WO 94/16062   7/1994   WIPO.

OTHER PUBLICATIONS

Kotzin et al., *Advances in Immunology*, vol. 54, pp. 99–166; 1993.
Albrecht et al., *J. Virol.* 66:5047; 1992.
Nicholas et al., *Virol.* 179:189; 1990.
Thompson and Nicholas, *Nature* 351:530;1991.
Choi et al., *Nature* 350:203; 1991.
Albrecht et al., *Virol.* 174:533; 1990.
Sambrook et al., "The Effects of Length and Degeneracy of the Oligonucleotide on the Specificity of Hybridization," In: Molecular Cloning, A Laboratory Manuel, Second Edition, Cold Spring Harbor Laboratory Press, pp. 11.7–11.8, 1989.
Kotzin et al., "Superantigens and Their Potential Role in Human Diseases," Adv. Immunol. 54: 99–166 (1993).

*Primary Examiner*—Michael P. Woodward
*Assistant Examiner*—Jay Williams
*Attorney, Agent, or Firm*—Patricia Anne Perkins

[57] ABSTRACT

Isolated viral proteins, and compositions made therefrom, are disclosed which are capable of binding to Class II Major Histocompatibility Complex antigen, thereby functioning to inhibit an antigen-specific response. The isolated viral proteins also act as superantigens.

10 Claims, 5 Drawing Sheets

MALDLRNLKHLTANFSFRIMIWIMLCLALPTDSKPISTTEAPILNITQSP

SLNISSPSTLEPSEPLKNCTTFLDLLWQRLGENASIKDLMLTLQREEVHG

RMTTLPSPRPSSKVEEQQLQRPRNLLPTAVGPPHVKYRLYNRLWEAPKGA

DVNGKPIQFDDPPLPYTGAYNDDGVLMVNINGKHVRFDSLSYWERIKRSG

TPWCIKTPSEKAAILKQLLKAEKKCRTTSKRITELEEQIKELEKTSTSP

Figure 1

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 249 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i i ) IMMEDIATE SOURCE:
        ( B ) CLONE: HVS14

( x i ) SEQUENCE DESCRIPTION: SEQ ID NO:1:

| Met | Ala | Leu | Asp | Leu | Arg | Asn | Leu | Lys | His | Leu | Thr | Ala | Asn | Phe | Ser |
|---|---|---|---|---|---|---|---|---|---|---|---|---|---|---|---|
| 1 | | | | 5 | | | | | 10 | | | | | 15 | |

| Phe | Arg | Ile | Met | Ile | Trp | Ile | Met | Leu | Cys | Leu | Ala | Leu | Pro | Thr | Asp |
|---|---|---|---|---|---|---|---|---|---|---|---|---|---|---|---|
| | | | 20 | | | | 25 | | | | | 30 | | | |

```
           Ser   Lys   Pro   Ile   Ser   Thr   Thr   Glu   Ala   Pro   Ile   Leu   Asn   Ile   Thr   Gln
                       35                            40                            45

Ser   Pro   Ser   Leu   Asn   Ile   Ser   Ser   Pro   Ser   Thr   Leu   Glu   Pro   Ser   Glu
                       50                            55                            60

Pro   Leu   Lys   Asn   Cys   Thr   Thr   Phe   Leu   Asp   Leu   Leu   Trp   Gln   Arg   Leu
           65                            70                            75                            80

Gly   Glu   Asn   Ala   Ser   Ile   Lys   Asp   Leu   Met   Leu   Thr   Leu   Gln   Arg   Glu
                                   85                            90                            95

Glu   Val   His   Gly   Arg   Met   Thr   Thr   Leu   Pro   Ser   Pro   Arg   Pro   Ser   Ser
                             100                           105                           110

Lys   Val   Glu   Glu   Gln   Gln   Leu   Gln   Arg   Pro   Arg   Asn   Leu   Leu   Pro   Thr
                             115                           120                           125

Ala   Val   Gly   Pro   Pro   His   Val   Lys   Tyr   Arg   Leu   Tyr   Asn   Arg   Leu   Trp
                       130                           135                           140

Glu   Ala   Pro   Lys   Gly   Ala   Asp   Val   Asn   Gly   Lys   Pro   Ile   Gln   Phe   Asp
                       145                           150                           155                     160

Asp   Pro   Pro   Leu   Pro   Tyr   Thr   Gly   Ala   Tyr   Asn   Asp   Asp   Gly   Val   Leu
                                   165                           170                           175

Met   Val   Asn   Ile   Asn   Gly   Lys   His   Val   Arg   Phe   Asp   Ser   Leu   Ser   Tyr
                             180                           185                           190

Trp   Glu   Arg   Ile   Lys   Arg   Ser   Gly   Thr   Pro   Trp   Cys   Ile   Lys   Thr   Pro
                       195                           200                           205

Ser   Glu   Lys   Ala   Ala   Ile   Leu   Lys   Gln   Leu   Leu   Lys   Ala   Glu   Lys   Lys
                       210                           215                           220

Cys   Arg   Thr   Thr   Ser   Lys   Arg   Ile   Thr   Glu   Leu   Glu   Glu   Gln   Ile   Lys
           225                           230                           235                           240

Glu   Leu   Glu   Lys   Thr   Ser   Thr   Ser   Pro
                             245
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Mouse ( v i i ) IMMEDIATE SOURCE:
        ( B ) CLONE: IL-7 signal peptide ( x i ) SEQUENCE DESCRIPTION: SEQ ID NO:2:

```
Met   Phe   His   Val   Ser   Phe   Arg   Tyr   Ile   Phe   Gly   Ile   Pro   Pro   Leu   Ile
                        5                            10                           15

Leu   Val   Leu   Leu   Pro   Val   Thr   Ser   Ser
                  20                      25
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: FLAG_ peptide (xi) SEQUENCE DESCRIPTION: SEQ ID NO:3:

Asp Tyr Lys Asp Asp Asp Asp Lys
1               5

(2) INFORMATION FOR SEQ ID NO:4:

(i) SEQUENCE CHARACTERISTICS:
        (A) LENGTH: 212 amino acids
        (B) TYPE: amino acid
        (D) TOPOLOGY: linear (ii) MOLECULE TYPE: protein (vi) ORIGINAL SOURCE:
        (A) ORGANISM: Human (vii) IMMEDIATE SOURCE:
        (B) CLONE: IgG1 Fc (xi) SEQUENCE DESCRIPTION: SEQ ID NO:4:

```
Arg Ser Cys Asp Lys Thr His Thr Cys Pro Pro Cys Pro Ala Pro Glu
1               5                   10                  15
Leu Leu Gly Gly Pro Ser Val Phe Leu Phe Pro Pro Lys Pro Lys Asp
                20                  25                  30
Thr Leu Met Ile Ser Arg Thr Pro Glu Val Thr Cys Val Val Val Asp
            35                  40                  45
Val Ser His Glu Asp Pro Glu Val Lys Phe Asn Trp Tyr Val Asp Gly
        50                  55                  60
Val Glu Val His Asn Ala Lys Thr Lys Pro Arg Glu Glu Gln Tyr Asn
65                      70                  75                  80
Ser Thr Tyr Arg Val Val Ser Val Leu Thr Val Leu His Gln Asp Trp
                    85                  90                  95
Leu Asn Gly Lys Glu Tyr Lys Cys Lys Val Ser Asn Lys Ala Leu Pro
                100                 105                 110
Ala Pro Ile Glu Lys Thr Ile Ser Lys Ala Lys Gly Gln Pro Arg Glu
            115                 120                 125
Pro Gln Val Tyr Thr Leu Pro Pro Ser Arg Asp Glu Leu Thr Lys Asn
        130                 135                 140
Gln Val Ser Leu Thr Cys Leu Val Lys Gly Phe Tyr Pro Ser Asp Ile
145                 150                 155                 160
Ala Val Glu Trp Glu Ser Asn Gly Gln Pro Glu Asn Asn Tyr Lys Thr
                165                 170                 175
Thr Pro Pro Val Leu Asp Ser Asp Gly Ser Phe Phe Leu Tyr Ser Lys
            180                 185                 190
Leu Thr Val Asp Lys Ser Arg Trp Gln Gln Gly Asn Val Phe Ser Cys
        195                 200                 205
Ser Val Met His
210
```

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (vii) IMMEDIATE SOURCE:
        (B) CLONE: Polylinker (xi) SEQUENCE DESCRIPTION: SEQ ID NO:5:

-continued

```
Gly  Gly  Gly  Gly  Ser  Gly  Gly  Gly  Gly  Ser  Gly  Gly  Gly  Gly
 1              5                         10
```

(2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (vii) IMMEDIATE SOURCE:
        (B) CLONE: Trimeric Leucine Zipper (xi) SEQUENCE DESCRIPTION: SEQ ID NO:6:

```
Arg  Met  Lys  Gln  Ile  Glu  Asp  Lys  Ile  Glu  Glu  Ile  Leu  Ser  Lys  Ile
 1              5                        10                       15

Tyr  His  Ile  Glu  Asn  Glu  Ile  Ala  Arg  Ile  Lys  Lys  Leu  Ile  Gly  Glu
              20                        25                       30

Arg
```

(2) INFORMATION FOR SEQ ID NO:7:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (vii) IMMEDIATE SOURCE:
        (B) CLONE: Dimeric Leucine Zipper (xi) SEQUENCE DESCRIPTION: SEQ ID NO:7:

```
Arg  Met  Lys  Gln  Leu  Glu  Asp  Lys  Val  Glu  Glu  Leu  Leu  Ser  Lys  Val
 1              5                        10                       15

Tyr  His  Leu  Glu  Asn  Glu  Val  Ala  Arg  Leu  Lys  Lys  Leu  Val  Gly  Glu
              20                        25                       30

Arg
```

ISOLATED *HERPESVIRUS SAIMIRI* PROTEINS THAT BIND MHC CLASS II MOLECULES

CROSS REFERENCE TO RELATED APPLICATION

This application is a continuation-in-part application of U.S. patent application Ser. No. 08/351,901, filed Dec. 7, 1994, now pending.

TECHNICAL FIELD OF THE INVENTION

The present invention relates generally to the field of viral proteins, and more specifically to viral proteins having immunoregulatory activity.

BACKGROUND OF THE INVENTION

Herpesvirus Saimiri (HVS) is a double-stranded DNA virus with tropism for T lymphocytes. It is ubiquitous in its natural host, the squirrel monkey, but is extremely oncogenic in a number of other primate species and in rabbits (Fleckenstein and Desrosiers, in *The Herpesviruses;* I. B. Roizman, ed.; Plenum Publishing Press, NY; pg. 253). The complete nucleotide sequence of the genome of HVS has been reported (Albrecht et al., *J. Virol.* 66: 5047; 1992); 83 potential genes were identified, including 76 major open reading frames (ORFs) and seven U-RNA genes.

Nicholas et al. (*Virol.* 179: 1 89; 1990) present the sequence of an immediate-early (IE) gene in the Hind III-G fragment of HVS which contains a region that exhibits similarity to a portion of a ORF in the long terminal repeat (LTR) of mouse mammary tumor virus (MMTV). Overall, this HVS ORF (designated HVS14 by Albrecht et al.) displayed approximately 25% identity and 46% similarity to the product of the Mls gene of MMTV (Thompson and Nicholas, Nature 351: 530; 1991). The Mls gene product is believed to act as a superantigen (Choi et at., Nature 350: 203; 1991).

None of the studies demonstrated the function of the protein predicted to be encoded in the HVS14 ORF; the low degree of homology renders it impossible to predict whether this protein acts as superantigen or not. Thus, prior to the present invention, there was a need in the art to establish the actual amino acid sequence and size of a protein encoded by the HVS14 ORF, and to determine the function of the protein.

SUMMARY OF THE INVENTION

The present invention identifies a protein encoded by an HVS ORF referred to as HVS14, which binds to Class II Major Histocompatibilty Complex (MHC) molecules. The present invention also provides a method for identifying and isolating such viral proteins. The viral proteins of the present invention can be used to regulate immune responses in a therapeutic setting; accordingly, pharmaceutical compositions comprising HVS14 proteins are also provided.

The isolated viral proteins of this invention are similar to the superantigen encoded by the Mls genes of certain retroviruses. The present invention specifically provides isolated HVS14 protein, in soluble form, as well as in native form. Deleted forms of HVS14 are also disclosed.

HVS14 binds Major Histocompatibility Complex (MHC) Class II molecules. MHC Class II complexes are known to be involved in antigen presentation, and in studies performed using the HVS14 fusion protein, HVS14 inhibited various antigen specific responses. Specifically, HVS14 inhibits antigen-specific proliferation of peripheral blood mononuclear cells. The present invention thus also provides a method of inhibiting undesirable antigen specific responses in a mammal. Such methods of inhibiting undesirable antigen specific responses are useful in preventing or treating autoimmune disease as well as tissue or organ transplant rejection, and in treatment or prevention of allergy or asthma.

The present invention also provides vital proteins expressed as fusion proteins. These and other aspects of the present invention will become evident upon reference to the following detailed description of the invention.

BRIEF DESCRIPTION OF THE DRAWINGS

FIG. 1 represents the amino acid sequence of the HVS14 protein. A hydrophobic region which may serve as a signal sequence. A potential cleavage site that would be useful if the hydrophobic region serves as a signal sequence falls between serine and lysine (^). Four potential glycosylation sites outside the hydrophobic region are in bold. The three cysteine residues outside the hydrophobic region are asterisked.

DETAILED DESCRIPTION OF THE INVENTION

Figure 2A:
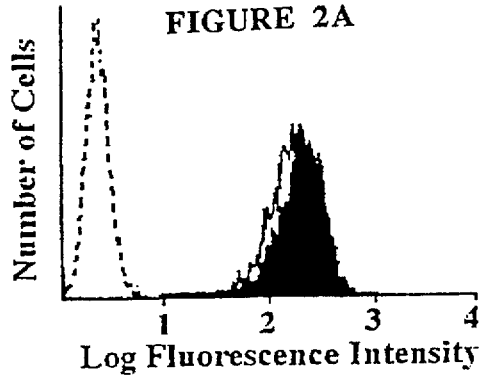
FIGS. 2A–2E illustrate inhibition of the binding of HVS14/Fc to HLA class II molecules by anti-class II antibodies or a soluble, full-length HVS14 protein. Preincubation of cells with anti-HLA DR monoclonal antibody inhibited 97% of HVS14 Fc binding to DG75 cells (FIG. 2b), whereas preincubation with anti-DP (FIG. 2c), anti-DQ (FIG. 2d) or anti-class I (FIG. 2a) monoclonal antibodies did not inhibit the HVS14 Fc binding. Full-length HVS14 also inhibited binding of HVS14/Fc (FIG. 2e).

Viral genomic DNA containing the HVS14 ORF was obtained and a soluble HVS14 protein was expressed in the form of a deletion mutant comprising an extracellular region of HVS14. The purified HVS14 deletion mutant inhibited antigen-specific responses, presumably by binding Class II α and β chains and interfering with antigen presentation. A soluble full length construct was also prepared, and acted as a superantigen, binding Class II α and β chains and stimulating T cell proliferation without processing by an antigen presenting cell. Additional soluble constructs comprising the extracellular region of HVS14 can be prepared and are expected to demonstrate the ability to bind Class II α and β chains. A detailed description of the invention and certain technical background information is presented below.

*Herpesvirus saimiri*

The herpesvirus family comprises enveloped, double stranded DNA viruses which infect various species and exhibit a propensity for establishing latent infections. *Her-*

*pesvirus saimiri* (HVS) is a member of the herpesvirus family which is ubiquitous in squirrel monkeys. There is little evidence that HVS is pathogenic for squirrel monkeys, however, infection of other species of monkeys such as marmosets results in malignant tumors of the lymphatic system. HVS and related viruses of other species are referred to as lymphocryptoviruses because the latent infections they establish involve lymphoid cells.

Transmission of HVS usually occurs horizontally, with infection of younger members of a colony by older members, probably through oral contact with virus-contaminated saliva or aerosol exposure of respiratory or conjunctival epithelium. Following the primary infection, HVS persists in white blood cells for years, often for the life of the host. In contrast to Epstein-Barr virus, a lymphocryptovirus that infects humans, HVS is T-lymphotropic.

In contrast to the native hosts, experimentally-infected marmosets die from a rapidly progressing neoplasia of the immune system. Upon autopsy, the organs of the reticuloendothelial systems usually exhibit extensive cellular infiltration. Persistent infection of susceptible marmosets with attenuated HVS does protect them from superinfection with wild-type virus. Other species of new world monkeys are also susceptible to neoplastic disease caused by HVS, although old world primates and humans appear to be resistant to this species of herpesvirus. HVS also causes lymphoproliferative disease in rabbits. Incidence of diseases in this animal model appears to be related to the type of rabbit used and the route of inoculation.

The genome of HVS consists of a light component (L-DNA) that is about 34.5% G+C, and is flanked by tandemly-repeated heavy components (H-DNA). According to the nomenclature of Albrecht et al., HVS ORFs are identified by a number representing their position within the L-DNA, and numbered from 01 to 76. The present invention relates to a protein encoded by HVS14, an ORF present on the complementary strand of the HVS genome, which encodes a putative peptide of 249 amino acids with a predicted molecular mass of 28.3 Kd.

HVS14

The complete nucleotide sequence of the genome of HVS has been reported (Albrecht et al., *J. Virol.* 66: 5047; 1992). Additional studies on one of the HVS open reading frames (ORFs), HVS14, are described in Nicholas et al., *Virol.* 179: 1 89; 1990. HVS14 is an immediate-early (IE) gene, and the mRNA message it encodes is detectable in cultures of infected cells immediately after removal of the protein synthesis inhibitor, cycloheximide, from the cultures. The HVS14 gene is present in the Hind III-G fragment of HVS, and contains a region that exhibits similarity to a portion of a ORF in the long terminal repeat (LTR) of mouse mammary tumor virus (MMTV). Overall, HVS14 displays approximately 25% identity and 46% similarity to the product of the Mls gene of MMTV (Thompson and Nicholas, *Nature* 351: 530; 1991), which is believed to act as a superantigen (Choi et al., *Nature* 350: 203; 1991). Other species of lymphocryptoviruses will have homologous ORFs that encode proteins similar to HVS14.

As described herein, a full length HVS14 protein was expressed, tested, and found to act as a superantigen. In contrast, an HVS14 deletion mutant that was missing the amino terminal 33 amino acids, and which was expressed in the form of an immunoglobulin Fc fusion protein, bound MHC Class II α and β chains and inhibited antigen presentation. HVS14 proteins will thus be useful regulating an immune responses in a therapeutic setting. HVS14 proteins that bind Class II α and β chains but that do not act as superantigens (HVS14 Class II binding proteins) are useful in inhibiting undesirable antigen specific responses in a mammal, for example, in preventing or treating autoimmune disease as well as tissue or organ transplant rejection, and in treatment or prevention of allergy or asthma.

HVS14 proteins that bind Class II α and β chains and act as superantigens (HVS14 Class II superantigen proteins) have utility in therapeutic regimens that require activation of a broad spectrum of T cells (as opposed to antigen-specific activation). Moreover, fusion proteins comprising HVS14 superantigen proteins and a heterologous protein that specifically binds to malignant cells will also be useful in treating cancer and viral disease in which viral antigens are expressed on host cells. For example, a fusion protein of staphylococcal enterotoxin A and a monoclonal antibody specific for human colon carcinoma cells, C215, inhibited tumor growth and allowed long-term survival of mice carrying B16 melanoma cells (Dohlstein et al., *Proc. Natl. Acad. Sci, USA* 91: 8845; 1994). Such useful fusion proteins can comprise antibodies, or molecules that specifically bind receptor or ligand proteins found on malignant cells (i.e., CD30), or that specifically bind to viral proteins. Furthermore, superantigens that functionally inactivate and delete certain peripheral T cells will also be useful in treating autoimmune conditions (see Kim et al., *J. Exp. Med.* 174: 1431, 1991).

HVS14 proteins are also useful as reagents in in vitro diagnostic assays. HVS14 superantigen proteins induce the proliferation of T cells, and can thus be used to develop and/or maintain specific T cell lines. Furthermore, there are many commercially available mitogens that are used to stimulate T cell proliferation in vitro; HVS14 superantigen proteins will also be useful in providing a reproducible source of such reagents. Similarly, HVS14 Class II binding proteins will have utility as reagents that block MHC class II antigen presentation in in vitro assays.

Superantigens

Superantigens bind to class II MHC molecules and to T cell receptors for antigens (TCR), cross-linking cells expressing MHC class II to cells expressing TCR. Binding to the TCR occurs through the variable region of the β chain of the TCR, referred to as Vβ. Unlike conventional antigens, superantigens do not require intracellular processing by antigen presenting cells in order to bind MHC class II. Superantigens also differ from conventional antigens in binding to a region of a class II molecule at a site other than the antigen binding cleft.

The proportion of T cells that proliferate in response to a superantigen can range from 5 to 25% of the T cells that encounter the superantigen. The high frequency of activation is accounted for by the binding of the superantigen to the Vβ region; virtually all T cells bearing a particular Vβ are activated upon binding of an appropriate superantigen. In contrast, for a primary antigen response against a particular (non-superantigen) foreign antigen, a markedly lower proportion of T cells responds, from about one in $10^4$ to one in $10^6$ T cells.

One type of superantigen, the minor lymphocyte stimulating (Mls) determinants, was first detected by the stimulation of a strong primary mixed-lymphocyte reaction between cells from mice of the same MHC haplotype. The Mls genes caused deletion of T cells that expressed certain Vβ chains (Kappler et al., *Nature* 332: 35, 1988; MacDonald et al., *Nature* 332: 40, 1988). Subsequent studies demonstrated that Mls determinants are actually encoded by an ORF of the 3' long terminal repeat of the MMTV genome (Choi et al., supra). A review of the various Mls determinants is presented by Acha-Orbea, *Immunol. Today* 12: 357, 1991.

Bacterial superantigens include the Staphylococcal enterotoxins (SE) and toxic shock syndrome toxin (TSST-1), *Streptococcus pyogenes* exotoxins (SPE-A, SPE-C, pep M5 and exfoliating toxin), and *Pseudomonas aeruginosa* exotoxin A. Other bacteria also produce toxins that appear to act as superantigens, including *Yersinia enterocolitica, Clostridium perfringens* and Mycobacterium spp. Rabies virus is also believed to encode a superantigen (Lafon et al., *Nature* 358: 507, 1992), as is Moloney murine leukemia virus (Hügin et al., *Science* 252: 424, 191). Several lines of evidence also indicate that a superantigen may be encoded by the Human Immunodeficiency Virus, and may be implicated in AIDS (reviewed in Irwin and Gascoigne, *J. Leukocyte Biol.* 54: 495; 1993).

The ability of superantigens to stimulate clonal deletion of T cells based on the Vβ expressed has stimulated study of the role of superantigens in self-tolerance, and in anergy (reviewed in Marrack et al., *Immunol. Rev.* 133: 119, 1993; MacDonald et al., *Immunol. Rev.* 133: 105, 1993; Herman et al., *Annu. Rev. Immunol.* 9: 745, 1991). Bacterial superantigens may cause some of the symptoms of food poisoning by activating macrophages or T cells (Johnson et al., *FASEB J.* 5: 2706, 1991; Marrack et al., *J. Exp. Med.* 171: 455, 1990). Furthermore, certain autoimmune diseases exhibit characteristics that implicate superantigens in their etiology (reviewed in Irwin and Gascoigne, supra).

MHC Class II antigens

Antigen presenting cells (APC), which include mononuclear phagocytes, certain dendritic cells such as Langerhans dendritic cells and follicular dendritic cells, and B cells, take up proteinaceous antigens and process them. Such processing can involve unfolding the protein or fragmentation (enzymatic and/or chemical) into smaller peptides. Processed antigens, or in the case of superantigens, unprocessed antigens, are then presented on the surface of the APC, in the form of a complex with the class II molecule. CD4+ T cells respond to APC bearing such antigen/class II complexes by proliferating and secreting lymphokines (including Interleukin-2 and Interferon-γ). Class II molecules are thus central to both the humoral and cellular branches of an immune response.

Peptide antigens bind to Class II molecules with varying affinity, and failure to respond to certain peptide antigens has been associated with the inability of particular Class II molecules to bind the peptide. The original identification of these molecules came from the discovery that allelic variations within the regions encoding MHC Class I (HLA-D region in humans and H-2I region in the mouse) resulted in stimulation in mixed lymphocyte cultures (MLC) in vitro, and led to graft rejections in vivo.

Class II antigens are composed of two non-covalently associated polypeptide chains designated α and β. The α chain is an acidic polypeptide with two external, structural domains and an approximate molecular weight of 25–33 kD. The β chain is a basic polypeptide of 24–29 kD in molecular weight, and also has two external structural domains. Both chains are glycosylated transmembrane proteins and contain a highly conserved region of ten to twelve peptides linking the membrane proximal domain to the hydrophobic transmembrane region. The higher molecular weight of the α chain is generally accounted for by the presence of two carbohydrate moieties, a complex type oligosaccharide and a high mannose type. The β chain contains a single complex type carbohydrate.

Additional information regarding the structure and function of MHC Class II antigens may be found in many general immunology textbooks (for example, *Fundamental Immunology*, Second Edition; W. E. Paul, Ed. Raven Press, 1993), as well as in descriptions of the numerous scientific studies that have been performed.

Proteins and Analogs

The present invention provides isolated HVS14 proteins having immunoregulatory activity. Such proteins are substantially free of contaminating endogenous materials and, optionally, without associated native-pattern glycosylation. Derivatives of the HVS14 proteins within the scope of the invention also include various structural forms of the primary protein which retain biological activity. Due to the presence of ionizable amino and carboxyl groups, for example, an HVS14 protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Other derivatives of the HVS14 protein within the scope of this invention include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of HVS14 proteins (e.g., poly-His). The amino acid sequence of the viral proteins can also be linked to an identification peptide such as that described by Hopp et al., *Bio/Technology* 6: 1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*.

Fusion proteins further comprise the amino acid sequence of an HVS14 protein linked to an immunoglobulin Fc region. An exemplary Fc region is a human IgG1 having a nucleotide and amino acid sequence set forth in SEQ ID NO:4. Fragments of an Fc region may also be used, as can Fc muteins such as those described in U.S. Ser. No. 08/145, 830, filed Oct. 29, 1993. Depending on the portion of the Fc region used, an HVS14 protein may be expressed as a dimer, through formation of interchain disulfide bonds. If HVS14 fusion proteins are made with both heavy and light chains of an antibody, it is possible to form a viral protein oligomer with as many as four HVS14 protein regions.

In another embodiment, HVS14 proteins further comprise a zipper domain. Exemplary zipper domains are described in U.S. Ser. No. 08/107,353, filed Aug. 13, 1993, the relevant disclosure of which is incorporated by reference herein. Examples of zipper domains are those found in the yeast transcription factor GCN4 and a heat-stable DNA-binding protein found in rat liver (C/EBP; Landschulz et al., *Science* 243: 1681, 1989), the nuclear transforming proteins, fos and jun, which preferentially form a heterodimer (O'Shea et al., *Science* 245: 646, 1989; Turner and Tjian, *Science* 243:

1689, 1989), and the gene product of the murine proto-oncogene, c-myc (Landschulz et al., *Science* 240: 1759, 1988). The fusogenic proteins of several different viruses, including paramyxovirus, coronavirus, measles virus and many retroviruses, also possess zipper domains (Buckland and Wild, *Nature* 338: 547, 1989; Britton, *Nature* 353: 394, 1991; Delwart and Mosialos, *AIDS Research and Human Retroviruses* 6: 703, 1990). Preferred zipper domains are represented in SEQ ID NOs:6 and 7; the zipper represented by SEQ ID NO:7 forms a homodimer.

HVS14 protein derivatives may also be used as immunogens, reagents in in vitro assays, or as binding agents for affinity purification procedures, for example, in purifying MHC Class II molecules. HVS14 protein derivatives may also be obtained by cross-linking agents, such as M-maleimidobenzoyl succinimide ester and N-hydroxysuccinimide, at cysteine and lysine residues. HVS14 proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the HVS14 protein or against other proteins which are similar to the viral protein, as well as other proteins that bind HVS14.

The present invention also includes HVS14 proteins with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of HVS14 DNAs in bacteria such as *E. coil* provides non-glycosylated molecules. Functional mutant analogs of HVS14 protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Set or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

HVS14 protein derivatives may also be obtained by mutations of the native viral proteins or its subunits. An HVS14 mutated protein, as referred to herein, is a polypeptide homologous to an HVS14 protein but which has an amino acid sequence different from the native viral protein because of one or a plurality of deletions, insertions or substitutions. The effect of any mutation made in a DNA encoding an HVS14 peptide may be easily determined by analyzing the ability of the mutated HVS14 peptide to bind its counter structure, MHC Class II molecules.

Bioequivalent analogs of viral proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

Generally, substitutions should be made conservatively; i.e., the most preferred substitute amino acids are those which do not affect the ability of the inventive proteins to bind their receptors in a manner substantially equivalent to that of native HVS14. Examples of conservative substitutions include substitution of amino acids outside of the binding domain(s), and substitution of amino acids that do not alter the secondary and/or tertiary structure of HVS14. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Similarly, when a deletion or insertion strategy is adopted, the potential effect of the deletion or insertion on biological activity should be considered. Subunits of viral proteins may be constructed by deleting terminal or internal residues or sequences to form fragments. Additional guidance as to the types of mutations that can be made is provided by a comparison of the sequence of HVS14 to the sequences and structures of other C-type lectin family members.

Mutations in nucleotide sequences constructed for expression of analog HVS14 proteins must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated viral proteins screened for the desired activity.

Not all mutations in the nucleotide sequence which encodes a viral protein will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42: 133, 1986); Bauer et al. (*Gene* 37: 73, 1985); Craik (*BioTechniques,* January 1985, 12–19); Smith et al. (*Genetic Engineering: Principles and Methods,* Plenum Press, 1981); and U.S. Pat. Nos. 4,518,584 and 4,737,462 disclose suitable techniques, and are incorporated by reference herein.

Due to code degeneracy, there can be considerable variation in nucleotide sequences encoding the same amino acid sequence. Other embodiments include sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding HVS14 proteins, and other sequences which are degenerate to those which encode the HVS14 proteins. DNAs which hybridize under stringent conditions (hybridization in 6×SSC at 63° C. overnight; washing in 3×SSC at 55° C.) are preferred. In a preferred embodiment, HVS14 analogs are at least about 70% identical in amino acid sequence to the amino acid sequence of HVS proteins as set forth in SEQ ID NO:1. In a most preferred embodiment, HVS14 analogs are at least about 80% identical in amino acid sequence to HVS proteins.

Percent identity may be determined using a computer program, for example, the GAP computer program described by Devereux et al. (*Nucl. Acids Res.* 12: 387, 1984) and available from the University of Wisconsin Genetics Computer Group (UWGCG). For fragments derived from the HVS14 protein, the identity is calculated based on that portion of the HVS14 protein that is present in the fragment.

Expression of Recombinant HVS14 Proteins

The proteins of the present invention are preferably produced by recombinant DNA methods by inserting a DNA sequence encoding HVS14 protein into a recombinant expression vector and expressing the DNA sequence in a recombinant microbial expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding HVS14 proteins or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding HVS14 proteins which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2: 95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275: 615, 1978; and Goeddel et al., *Nature* 281: 544, 1979), the tryptophan (trp) promoter system (Goeddel et al., *Nucl. Acids Res.* 8: 4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ls thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255: 2073, 1980) or other glycolytic enzymes (Hess et al., *J. Adv. Enzyme Reg.* 7: 149, 1968; and Holland et al., *Biochem.* 17: 4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258: 2674, 1982) and Beier et al. (*Nature* 300: 724, 1982). The yeast α-factor leader, which directs secretion of heterologous proteins, can be inserted between the promoter and the structural gene to be expressed. See, e.g., Kurjan et al., *Cell* 30: 933, 1982; and Bitter et al., *Proc. Natl. Acad. Sci. USA* 81: 5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273: 113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3: 280, 1983).

A useful system for stable high level expression of mammalian receptor cDNAs in C127 murine mammary epithelial cells can be constructed substantially as described by Cosman et al. (*Mol. Immunol.* 23: 935, 1986). A preferred eukaryotic vector for expression of HVS14 protein DNA is referred to as pDC406 (McMahan et al., *EMBO J.* 10: 2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the HVS origin of replication, is CV-1/EBNA (ATCC CRL 10478). The CV-1/EBNA cell line was derived by transfection of the CV-1 cell line with a gene encoding Epstein-Barr virus nuclear antigen-1 (EBNAo1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the HVS14 proteins of the present invention. Transformed host cells may express the desired HVS14 protein, but host cells transformed for purposes of cloning or amplifying viral DNA do not need to express the HVS14 protein. Expressed HVS14 proteins will preferably be secreted into the culture supernatant, depending on the DNA selected, but may be deposited in the cell membrane.

Suitable host cells for expression of viral proteins include prokaryotes, yeast or higher eukaryotic cells under the control of appropriate promoters. Prokaryotes include gram negative or gram positive organisms, for example *E. coli* or Bacillus spp. Higher eukaryotic cells include established cell lines of mammalian origin as described below. Cell-free translation systems could also be employed to produce viral proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual,* Elsevier, N.Y., 1985), the relevant disclosure of which is hereby incorporated by reference.

Prokaryotic expression hosts may be used for expression of HVS14 proteins that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium,* and various species within the genera Pseudomonas, Streptomyces, and Staphylococcus, although others may also be employed as a matter of choice.

Recombinant HVS14 proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding the viral protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75: 1929, 1978, selecting for Trp$^+$ transformants in a selective medium consisting of 0.67% yeast nitrogen base, 0.5% casamino acids, 2% glucose, 10 μg/ml adenine and 20 μg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6: 47 (1988). Examples of suitable mammalian host cell lines include the COS-7 lines of monkey kidney cells, described by Gluzman (*Cell* 23: 175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of HVS14 proteins

Purified HVS14 proteins or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein (i.e. MHC Class II molecules) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying HVS14.

Affinity chromatography is a particularly preferred method of purifying HVS14 proteins. For example, an HVS14 protein expressed as a fusion protein comprising an immunoglobulin Fc region can be purified using Protein A or Protein G affinity chromatography. Moreover, an HVS14 protein comprising a zipper domain may be purified on a resin comprising an antibody specific to the zipper domain. Monoclonal antibodies against the HVS14 protein may also be useful in affinity chromatography purification, by utilizing methods that are well-known in the art.

Finally, one or more reversed-phase high performance liquid chromatography (RP-HPLC) steps employing hydrophobic RP-HPLC media, e.g., silica gel having pendant methyl or other aliphatic groups, can be employed to further purify a viral protein composition. Some or all of the foregoing purification steps, in various combinations, can also be employed to provide a homogeneous recombinant protein.

Recombinant HVS14 protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant viral protein can be disrupted by any convenient method, including freeze-thaw cycling, sonication, mechanical disruption, or use of cell lysing agents.

Fermentation of yeast which express viral protein as a secreted protein greatly simplifies purification. Secreted recombinant protein resulting from a large-scale fermentation can be purified by methods analogous to those disclosed by Urdal et al. (J. Chromatog. 296: 171, 1984). This reference describes two sequential, reversed-phase HPLC steps for purification of recombinant human GM-CSF on a preparative HPLC column.

Viral protein synthesized in recombinant culture is characterized by the presence of non-viral cell components, including proteins, in amounts and of a character which depend upon the purification steps taken to recover the viral protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of HVS14 protein free of other proteins which may be normally associated with the HVS14 protein as it is found in nature in its species of origin.

Administration of HVS14 Protein Compositions

The present invention provides methods of using therapeutic compositions comprising an effective amount of a viral protein and a suitable diluent and carrier, and methods for regulating an immune response. The use of HVS14 proteins in conjunction with soluble cytokine receptors or cytokines, or other immunoregulatory molecules is also contemplated.

For therapeutic use, purified HVS14 protein is administered to a patient, preferably a human, for treatment in a manner appropriate to the indication. Thus, for example, HVS14 protein compositions administered to suppress immune function can be given by bolus injection, continuous infusion, sustained release from implants, or other suitable technique. Typically, a therapeutic agent will be administered in the form of a composition comprising purified HVS14 protein in conjunction with physiologically acceptable carriers, excipients or diluents. Such carriers will be nontoxic to recipients at the dosages and concentrations employed.

Ordinarily, the preparation of such HVS14 protein compositions entails combining the viral protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

HVS14 proteins can be administered for the purpose of preventing or inhibiting undesirable, antigen-specific immune or inflammatory responses. Exemplary conditions in which it is advantageous to inhibit such undesirable responses include autoimmune syndromes, including myasthenia gravis, multiple sclerosis and systemic lupus erythematosis, and others as described in U.S. Pat. No. 5,284,935. Antibodies to the murine equivalent of MHC Class II antigens have been shown to provide protection against development of autoimmune syndromes in various animal models (Sriram and Steinman, J. Exp. Med. 158: 1362, 1983; Steinman et al., Proc. Natl. Acad. Sci. USA 78: 111, 1981; Waldor et al., Proc. Natl. Acad. Sci. USA 80: 2713, 1983). Moreover, HVS14 compositions can also be useful to prevent or treat rejection of tissue and/or organ transplants. Other conditions for which HVS14 compositions can be useful include those which involve undesirable immune responses to foreign antigens, for example those which occur in allergy or asthma.

HVS14 proteins can also be administered for the purpose of acting as a superantigen, for example, in order to control disease activity in autoimmune syndromes. Injection of bacterial superantigen SEB into autoimmune MRL/lpr mice suppressed disease activity in a dose-dependent manner (Kim et al., J. Exp. Med. 174: 1431; 1991). HVS14 superantigens also have utility in therapeutic regimens that require activation of a broad spectrum of T cells, and fusion proteins comprising HVS14 superantigen proteins and a heterologous protein that specifically binds to malignant cells will also be useful in treating cancer and viral disease in which viral antigens are expressed on host cells.

Preparation of Fusion Proteins Comprising Viral Proteins

Soluble forms of some mammalian proteins have been expressed as fusion proteins in which an extracellular domain of a membrane protein is joined to an immunoglobulin heavy chain constant (Fc) domain (Gascoigne et al., Proc. Natl. Acad. Sci. U.S.A. 84: 2936, 1987; Sledziewski et al., European patent application 89100787.4, publication number 0 325 224, published Jul. 26, 1989; Fanslow et al., J. Immunol. 149: 65, 1992; Noelle et al., Proc. Natl. Acad. Sci. U.S.A. 89: 6550, 1992; Capon et al., U.S. Pat. No. 5,116,964, issued May 26, 1992; U.S. Ser. No. 07/969,703, filed Oct. 23, 1992; U.S. Ser. No. 07/966,775, filed Oct. 27, 1992; U.S. Ser. No. 07/977,693, filed Nov. 13, 1992; U.S. Ser. No. 08/097,827, filed Jul. 23, 1993; U.S. Ser. No. 08/106,507, filed Aug. 13, 1993; U.S. Ser. No. 08/111,758, filed Aug. 25, 1993; and U.S. Ser. No. 08/114,426, filed Aug. 30, 1993), or with an extracellular domain of murine T lymphocyte antigen CD8 (Hollenbaugh et al., *EMBO J.* 11: 4313, 1992). Such fusion proteins are useful as reagents to detect their cognate proteins. They are also useful as therapeutic agents in treatment of disease. Mutated Fc regions have also been used to prepare soluble forms of transmembrane proteins. Useful Fc muteins (mutated proteins) are described in U.S. Ser. No. 08/145,830, filed Oct. 29, 93, the relevant disclosure of which is hereby incorporated by reference.

Oligomerizing zipper (or zipper) is a term that is used to refer to a repetitive heptad motif present as a conserved domain in several proteins. Such zippers fold as short, parallel coiled coils, and are believed to be responsible for oligomerization of the proteins of which they form a domain. Sequences derived from the fos and jun zippers have been used in the formation of bispecific antibodies by expression of DNA encoding the $V_L$ and $V_H$ regions of antibodies as fusion proteins with the zipper sequences. (Kostelny et al., *J. Immunol.* 148: 1547, 1992) Zipper sequences have also been used to replace the dimerization domain of λ repressor, a soluble DNA-binding protein of bacteriophage λ (Hu et al., *Science* 250: 1400, 1990), and in the preparation of a dimeric form of MalE, a maltose binding protein of *E. coli* that is exported into the periplasmic space (Blondel and Bedoulle, *Protein Engineering* 4: 457, 1991). Oligomerizing zippers are described in U.S. Ser. No. 08/107,353, filed Aug. 13, 1993.

Fusion proteins comprising viral proteins may also be prepared. In addition to a viral protein, such fusion proteins will also comprise a fusion moiety such as an oligomerizing zipper or an immunoglobulin Fc region, as described above. The HVS14/Fc and HVS14/zipper proteins described in great detail herein are exemplary of soluble viral fusion proteins. Other exemplary viral proteins that will be useful in forming such soluble fusion proteins include poxvirus proteins such as T2, described in U.S. Ser. No. 07/963,330, filed Oct. 19, 1992; A53R, described in U.S. Ser. No. 08/089,458, filed Jul. 20, 1993; and two vaccinia virus proteins structurally related to the Interleukin-1 receptor (Smith and Chan, *J. Gen. Virol.* 72: 511; 1991). Additional poxvirus proteins may also be prepared; see for example Johnson et al. (*Virology* 196: 381; 1993) which discusses the known ORFs of vaccinia virus. Moreover, proteins encoded by other viruses such as HVS and other members of the Herpesvirus family are included among viral proteins which can form soluble fusion proteins.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes construction of an HVS14/Fc DNA construct to express a soluble HVS14-immunoglobulin Fc fusion protein referred to as HVS14/Fc. DNA encoding HVS14/Fc comprises sequences encoding a leader (or signal) peptide (murine IL-7 leader, SEQ ID NO: 2; Namen et al., *Nature* 333: 571, 1988), an octapeptide referred to as Flag® (SEQ ID NO: 3; Hopp et al., supra), a suitable Fc region of an immunoglobulin (SEQ ID NO:4; U.S. Ser. No. 07/969,703, filed Oct. 23, 1992), a flexible linker sequence (SEQ ID NO:5, or as described in U.S. Pat. No. 5,073,627, issued Dec. 17, 1991) and the extracellular region of HVS14 from amino acid 34 to amino acid 249 (SEQ ID NO:1). An expression vector containing a leader sequence, and human IgG$_1$ Fc is prepared using conventional techniques of enzyme cutting and ligation of fragments encoding a leader sequence, and the human IgG$_1$ Fc, followed by a flexible linker sequence. The resulting vector is then restricted with Bspe1 and Not 1.

A PCR technique (Saiki et al., *Science* 239: 487, 1988) was employed using 5' (upstream) and 3' (downstream) oligonucleotide primers to amplify the DNA sequences encoding HVS14 extracellular ligand binding domain from viral genomic DNA (*J. Virol.* 66: 5047; 1992) which contains the HVS14 ORF, to form a PCR fragment. The upstream oligonucleotide primer introduced a BspE1 site upstream from the extracellular domain of HVS14 (amino acids 34 through 249 of SEQ ID NO: 1). A downstream oligonucleotide primer introduced a Not 1 site just downstream of the termination codon of the HVS14. The PCR fragment was cut and then ligated into the expression vector containing a leader sequence, human IgG$_1$ Fc and flexible linker sequence. The resultant DNA construct (HVS14/Fc) was transfected into the monkey kidney cell line CV-1/EBNA (ATCC CRL 10478). The construct encoded a soluble HVS14/Fc protein which was purified from large scale cultures of transfected CV-1/EBNA cells by affinity chromatography, ass described herein.

EXAMPLE 2

This example describes the binding of HVS14 Protein to MHC class II molecules. A panel of established including cell lines such as Daudi (Burkitt's lymphoma), DG75 (EBV-transformed B cell line), L-428 (Hodgkin's cell line), Jurkat (T cell leukemia cell line), and JB-6 (large anaplastic lymphoma, T cell type), were grown in RPMI 1640 supplemented with 10% FCS, 50 U/ml penicillin, 50 µg/ml streptomycin, 2 mM glutamine and $5 \times 10^{-5}$M 2-ME. These cells were used for FACS staining using soluble HVS14/Fc protein. Approximately $1 \times 10^6$ cells were preincubated on ice for 30 minutes in 100 µl of FACS buffer (PBS, 1% FCS and 0.1% NaN3) containing 2% normal goat serum and 2% normal rabbit serum to block nonspecific binding. 100 µl of HVS14/Fc or control Fc protein was added at 5 µg/ml and incubated on ice for 30 min. After washing, the cells were stained with biotin-labeled anti-human IgG (Fc specific) followed by PE-conjugated streptavidin (Becton Dickinson & Co., Mountain View, Calif.) in 100 µl of FACS buffer. Cells were then washed and analyzed using a FACScan (Becton Dickinson). A minimum of 5,000 cells was analyzed for each sample. The results (presented as the channel number of mean fluorescence intensity; Table 1) demonstrated that HVS14/Fc fusion protein binds to MHC class II positive cell lines, but not to class II negative cell lines.

TABLE 1

Binding of HVS14/Fc to Cell Lines

| | HLA Expression* | | | | | HVS14/Fc Binding | |
| | Negative Control | Anti class I ABC | Anti class II DR | Anti class II DP | Anti class II DQ | Control Fc protein | HVS14/ Fc |
|---|---|---|---|---|---|---|---|
| DG-75 | 3 | 964 | 542 | 178 | 36.5 | 3 | 406 |
| L-428 | 4 | 4 | 184 | 56 | 25 | 5 | 112 |
| K-299 | 3 | 487 | 649 | 392 | 136 | 3 | 352 |
| Jurkat | 3 | 228 | 3 | 3 | 3 | 3 | 3 |
| CEM | 3 | 523 | 5 | 4 | 4 | 2 | 3 |
| JB-6 | 2 | 205 | 3 | 2 | 2 | 3 | 3 |
| Daudi | 3 | 6 | 421 | 165 | 264 | 2 | 198 |

*HLA expression was determined by immunofluorescence using HLA-specific monoclonal antibodies.

Figure 2B:
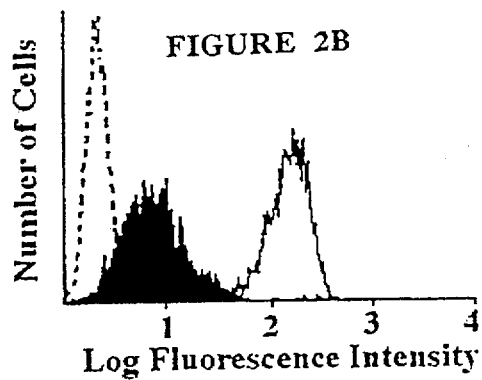
Figure 2C:
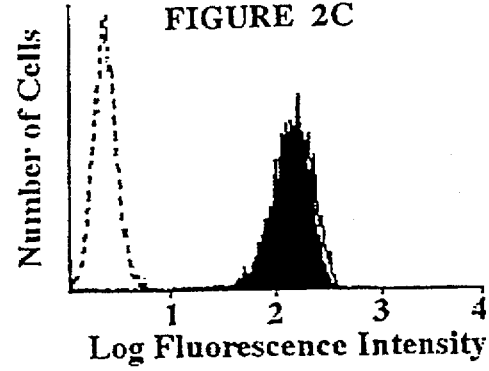
Figure 2D:
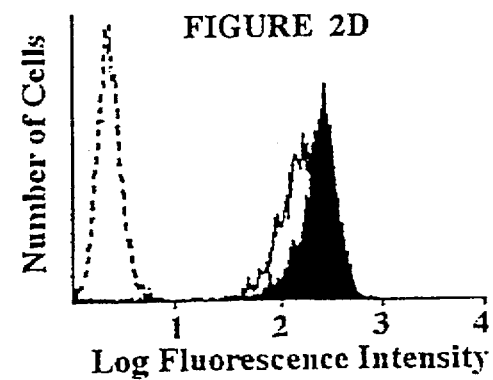
Figure 2E:
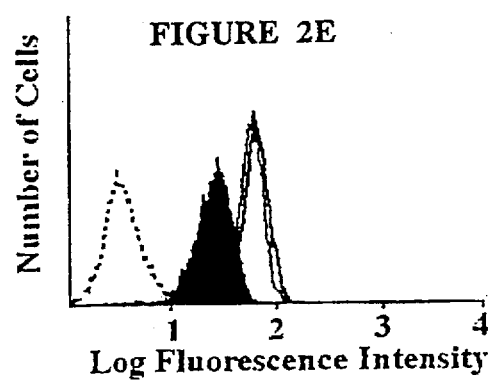

To demonstrate that the binding of HVS14/Fc to these cell lines is through MHC class II molecules, antibody inhibition experiments were performed. Cells were preincubated with 20 µg/ml of antibodies to MHC class II (Becton Dickinson) at 4° C. for 1 hr before the addition of HVS14/Fc protein. Cells were subsequently stained as described above. The results were shown in FIG. 2. Preincubation of cells with anti-HLA DR monoclonal antibody inhibited 97% of HVS14 Fc binding to DG75 cells (FIG. 2b), whereas preincubation with anti-DP (FIG. 2c), anti-DQ (FIG. 2d) or anti-class I (FIG. 2a) monoclonal antibodies did not inhibit the HVS14 Fc binding.

To demonstrate that the full length HVS14 can also bind to MHC class II, an inhibition experiment was performed using full-length HVS14 transfected supernatants to inhibit binding of the cells with HVS14/Fc. The results were shown in FIG. 2e. These results demonstrated that the full length native form HVS14, like HVS14/Fc fusion protein, was able to bind MHC class II DR molecules on the cell surfaces.

Direct binding of HVS14/Fc to MHC class II molecules were assessed using a slide binding assay, substantially as described by Gearing et al. (*EMBO J.* 8: 3667, 1989). Adherent CV1/EBNA cells were cultured on microslides, and transfected with the MHC class II α, β or α plus β chains. Two days later, cells were washed with binding medium containing 5% dry milk, and incubated with 1 µg/ml of HVS14/Fc protein, control Fc protein or 1 µg/ml of the monoclonal antibodies previously described. Subsequently, cells were washed, incubated with $^{125}$I-labeled goat anti-human IgG, or sheep anti-mouse IgG (New England Nuclear, Cambridge, Mass.). Cells were washed with binding medium followed by PBS, fixed in PBS containing 2.5% glutaraldehyde, washed again with PBS and air dried. The chamber slides were then dipped in Kodak GTNB-2 photographic emulsion and exposed for two days at 4° C. before developing. The results are shown in Table 2. HVS14/Fc specifically bound to cells transfected with both MHC class II α and β chains.

TABLE 2

Binding of HVS14 Fc to CV1/EBNA cells transfected with MHC class IIα and β chains

| | Vector | α chain | β chain | α + β chains |
|---|---|---|---|---|
| Control Fc | – | – | – | – |
| HVS14 Fc | – | – | – | +++ |
| mAbs | – | +++ | ++ | +++ |

EXAMPLE 3

This example describes construction of an HVS14 DNA construct to express a soluble HVS14 fusion protein referred to as trimeric HVS14. Trimeric HVS14 comprises a leader sequence, and a 33 amino acid sequence referred to as a "trimeric oligmerizing zipper" (SEQ ID NO:6; U.S. Ser. No. 07/969,703, filed Oct. 23, 1992), followed by the extracellular region of HVS14 from amino acid 34 to amino acid 249 (SEQ ID NO:1). The 33 amino acid sequence presented in SEQ ID NO:6 trimerizes spontaneously in solution. Fusion proteins comprising this 33 amino acid sequence are thus expected to form trimers or multimers spontaneously.

The construct is prepared by synthesizing oligonucleotides representing a leader sequence, and the 33 amino acid sequence described above, then ligating the final product to a DNA fragment encoding amino acids 34 through 249 of SEQ ID NO:1, prepared as described in Example 1.

The resulting ligation product in expression vector pDC409 was transfected into the monkey kidney cell line CV-1/EBNA (ATCC CRL 10478). pDC409 differs from pDC406 in that a Bgl II restriction site outside of the multiple cloning site has been deleted, making the Bgl II site within the multiple cloning site unique.

Once cells expressing the fusion construct are identified, large scale cultures of transfected cells are grown to accumulate supernatant from cells expressing trimeric HVS14. The trimeric HVS14 fusion protein in supernatant fluid is purified by conventional protein purification methods; silver-stained SDS gels of the eluted HVS14 fusion protein can be prepared to determine purity.

EXAMPLE 4

This example describes construction of an HVS14 DNA construct to express a soluble HVS14 fusion protein referred to as dimeric HVS14. Dimeric HVS14 contains a leader sequence, and a 33 amino acid sequence referred to as a "dimeric oligmerizing zipper" (SEQ ID NO:7), followed by the extracellular region of HVS14 from amino acid 34 to amino acid 249 (SEQ ID NO:1). The 33 amino acid sequence presented in SEQ ID NO:7 is derived from the yeast GCN4 leucine zipper sequence (O'Shea et al., *Science* 243: 538, 1989; Harbury et al., *Science* 262: 1401, 1993), and forms a homodimer. Fusion proteins comprising this 33 amino acid sequence are thus expected to form homodimers spontaneously. The construct is prepared by synthesizing oligonucleotides representing a leader sequence, and the 33 amino acid sequence described above, then ligating the final product to a DNA fragment encoding amino acids 34 through 29 of SEQ ID NO:1, prepared as described in Example 1.

The resulting ligation product in a suitable expression vector (for example, pDC406) is transfected into the monkey kidney cell line CV-1/EBNA (ATCC CRL 10478). The pDC406 plasmid includes regulatory sequences derived from SV40, human immunodeficiency virus (HIV), and Epstein-Barr virus (HVS). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the HVS origin of replication.

Once cells expressing the fusion construct are identified, large scale cultures of transfected cells are grown to accumulate supernatant from cells expressing dimeric HVS14. The dimeric HVS14 fusion protein in supernatant fluid is purified by using conventional protein purification methods, for example by one ore more steps utilizing ion exchange chromatography, size exclusion chromatography, or chromatography using hydrophobic interaction as a purification means. Affinity chromatography, for example using an antibody to HVS14 or an antibody to the oligmerizing zipper sequence, are also useful, as is reverse-phase HPLC. Silver-stained SDS gels of the dimeric HVS14 fusion protein can be prepared to determine purity.

EXAMPLE 5

This example describes construction of an HVS14 DNA construct to express a soluble HVS14 protein referred to as monomeric HVS14. Monomeric HVS14 contains a leader sequence, and the extracellular region of HVS14 from amino acid 34 to amino acid 249 (SEQ ID NO:1). The construct is prepared essentially as described for other soluble constructs, by ligating a DNA fragment encoding amino acids 34 through 249 of SEQ ID NO:1 (prepared as described in Example 1) into an appropriate expression vector which contains a suitable leader sequence. The resultant DNA construct is transfected into a suitable cell line such as the monkey kidney cell line CV-1/EBNA (ATCC CRL 10478). Monomeric HVS14 may be purified and analyzed using any of the methods described herein.

EXAMPLE 6

This example describes construction of an HVS14 DNA construct to express a full length HVS14. A PCR technique (Saiki et al., *Science* 239: 487, 1988) was employed using 5' (upstream) and 3' (downstream) oligonucleotide primers to amplify the DNA sequences encoding full-length HVS14 from viral genomic DNA (*J. Virol.* 66: 5047; 1992) which contains the HVS14 ORF, to form a PCR fragment. The upstream oligonucleotide primer introduced a Sal 1 site upstream from the initiation codon of HVS14; the downstream oligonucleotide primer introduced a Not 1 site just downstream of the termination codon of the HVS14. The resulting PCR fragment was then ligated into an expression vector cut with Sal I/Not I. The resultant DNA construct (flHVS14) is transfected into a suitable cell line such as the monkey kidney cell line CV-1/EBNA (ATCC CRL 10478), and is purified and analyzed using any of the methods described herein.

EXAMPLE 7

This example describes purification of HVS14 fusion proteins. HVS14/Fc fusion protein is purified by conventional methods using Protein A or Protein G chromatography. Approximately one liter of culture supernatant containing HVS14/Fc fusion protein is purified by filtering mammalian cell supernatants (e.g., in a 0.45 m filter) and applying filtrate to a protein A/G antibody affinity column (Schleicher and Schuell, Keene, N.H.) at 4° C. at a flow rate of 80 ml/hr for a 1.5 cm×12.0 cm column. The column is washed with 0.5M NaCl in PBS until free protein is not detected in the wash buffer. Finally, the column is washed with PBS. Bound fusion protein is eluted from the column with 25 mM citrate buffer, pH 2.8, and brought to pH 7 with 500 mM Hepes buffer, pH 9.1.

An HVS14 fusion protein comprising Flag® may also be detected and/or purified using an antibody that binds Flag®, substantially as described in Hopp et al., *Bio/Technology* 6: 1204 (1988). Moreover, a HVS14 protein comprising a poly-His peptide may be detected and/or purified using a poly-His system, substantially as described in U.S. Pat. No. 5,284,933, issued Feb. 8, 1994. MHC Class II binding is used as an assay for detection of HVS14 activity. Biological activity is measured in any biological assay which quantifies an antigen-specific immune response, for example, as described in Examples 9 through 12 herein.

EXAMPLE 8

This example illustrates the preparation of monoclonal antibodies against HVS14. Preparations of purified recombinant HVS14, for example, or transfected cells expressing high levels of HVS14, are employed to generate monoclonal antibodies against HVS14 using conventional techniques, such as those disclosed in U.S. Pat. No. 4,411,993. Such antibodies are likely to be useful in interfering with HVS14 binding to MHC Class II antigens, as components of diagnostic or research assays for HVS14, or in affinity purification of HVS14.

To immunize rodents, HVS14 immunogen is emulsified in an adjuvant (such as complete or incomplete Freund's adjuvant, alum, or another adjuvant, such as Ribi adjuvant R700 (Ribi, Hamilton, Mont.) or TiterMax (Vector Inc., Norcross, Ga.), and injected in amounts ranging from 10–100 μg subcutaneously into a selected rodent, for example, BALB/c mice or Lewis rats. Ten days to three weeks days later, the immunized animals are boosted with additional immunogen and periodically boosted thereafter on a weekly, biweekly or every third week immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable, for example, FACS analysis using cells expressing membrane-bound HVS14. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with HVS14, for example, by adaptations of the techniques disclosed by Engvall et al., *Immunochem.* 8: 871 (1971) and in U.S. Pat. No. 4,703,004. A preferred screening technique is the antibody capture technique described by Beckman et al., *J. Immunol.* 144: 4212 (1990). Hybridoma clones can also be screened or further analyzed by such techniques as Western blot, immunoprecipitation, FACS analysis, inhibition or augmentation of binding or biological activity, or other suitable assays. Positive clones are then injected into the peritoneal cavities of syngeneic rodents to produce ascites containing high concentrations (>1 mg/ml) of anti-HVS14 monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to HVS14 protein.

EXAMPLE 9

Figure 3A:
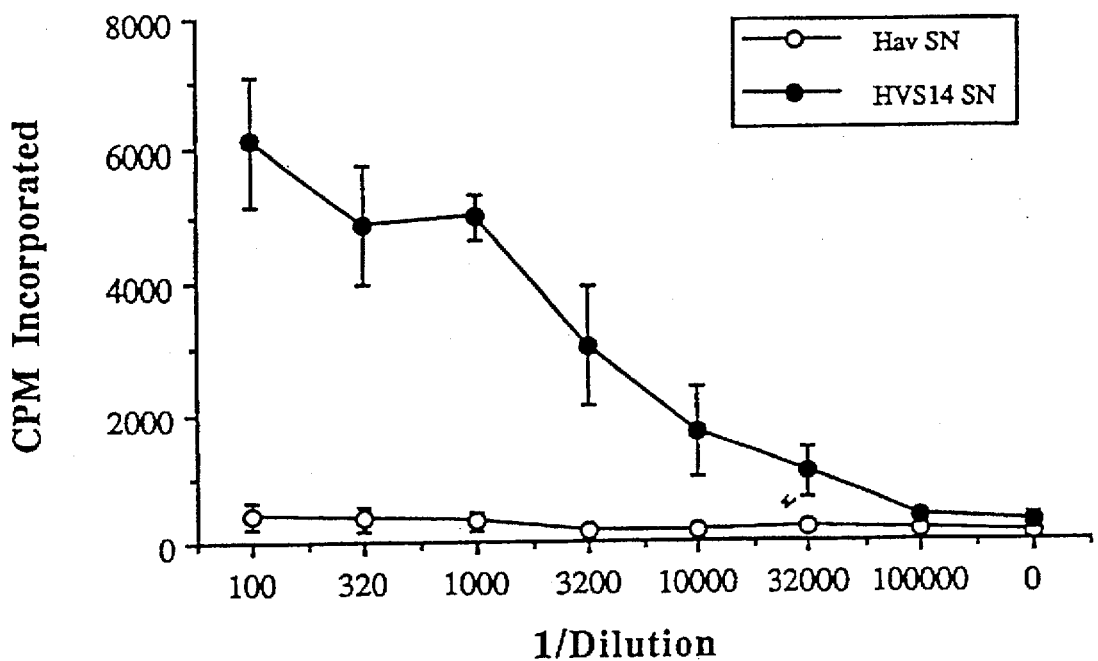
FIGS. 3A–3B demonstrate that recombinant, full-length HVS14 protein induces proliferation of normal human PBMCs in a dose dependent manner, in contrast to control supernatants from cells transfected with vector only.
Figure 3B:
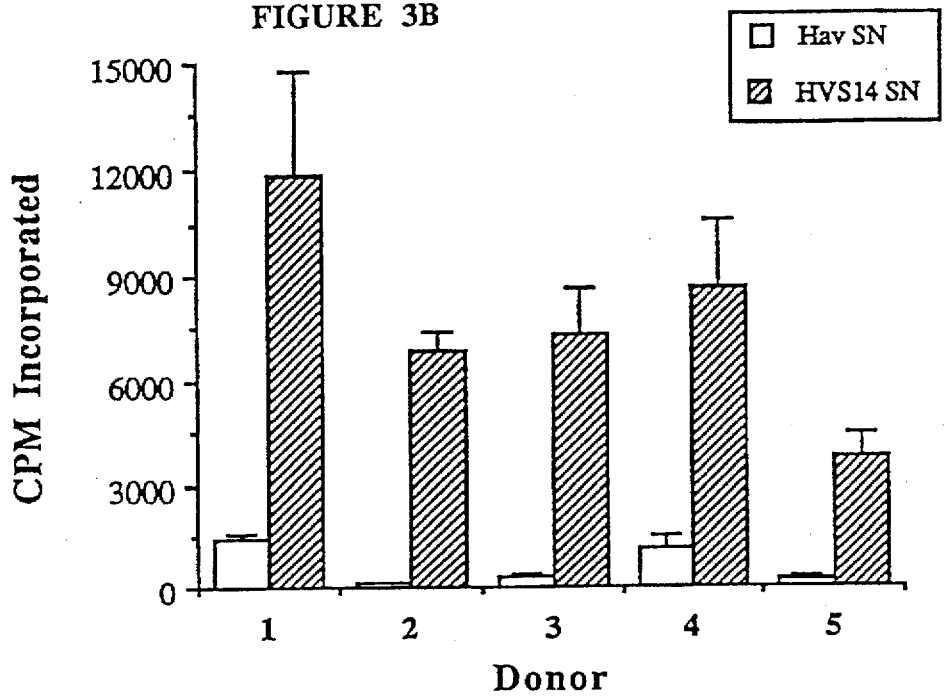

This example describes the ability of recombinant, full-length HVS14 protein to induce proliferation of normal human PBMCs. PBMCs were isolated from a healthy donor by centrifugation of heparinized blood over Isolymph (Gallard-Schlesinger Industries, Inc., Norway) and washed three times with culture medium. Culture medium consisted of RPMI 1640 supplemented with 10% FCS, 50 U/ml penicillin, 50 µg/ml streptomycin, 2 mM glutamine and $5 \times 10^{-5}$M 2-ME. PBMCs (approximately $1 \times 10^5$/well) were stimulated with either HVS14 transfected supernatant or control supernatant in culture medium in 96-well plates. After 5 to 9 days at 37° C., 1 µCi/well of [$^3$H] thymidine (Amersham Chemical Corp., Arlington Heights, Ill.) was added for 16 hours. Representative results are shown in FIG. 3. In contrast to control supernatants from cells transfected with vector only, HVS14 transfected supernatants induced proliferation of PBMCs in a dose dependent manner. Furthermore, two monoclonal antibodies against HVS14 inhibited the HVS14 induced proliferation of PBMC in a dose-dependent manner, whereas control monoclonal antibody did not.

EXAMPLE 10

This example illustrates the ability of HVS14 to stimulate PBMC proliferation without the requirement for antigen processing. PBMCs were isolated as described above, and separated into T cell and non-T-cell fractions by rosetting with 2-aminoethylisothiouronium bromide (AET)-treated sheep red blood cells. These twice rosetted cells were then suspended in RPMI 1640 culture media with 10% FCS and incubated on plastic dishes for 1 hr at 37° C. to remove any remaining adherent cells. The resulting cell preparations were always at least 98% T cells as determined by flow cytometric analysis (FACScan, Becton Dickinson & Co., Mountain View, Calif.). Monocyte-enriched cells were isolated from the non-T cell fraction by adherence to plastic dishes. Nonadherent cells were removed by washing the plates with warm complete media. Whole PBMCs were fixed with 0.2% paraformaldehyde for 5 minutes at room temperature, followed by quenching of the reaction with 0.15M Tris, pH 7,2, then washed four times with complete media. Fixed mononuclear cells were added as antigen presenting cells (APCs) at about $1 \times 10^5$ cells/ml, as were purified T cells. Proliferation was determined as described above. The results demonstrated that chemical fixation of APCs had little effect on presentation of HVS14 to T cells. In contrast, the T cell response to tetanus toxoid, an antigen that normally requires processing, was nearly abolished by fixation of the APCs. Therefore, the HVS14 protein responsible for the proliferation does not require processing, indicting that HVS14 functions as a superantigen.

EXAMPLE 11

Figure 4:
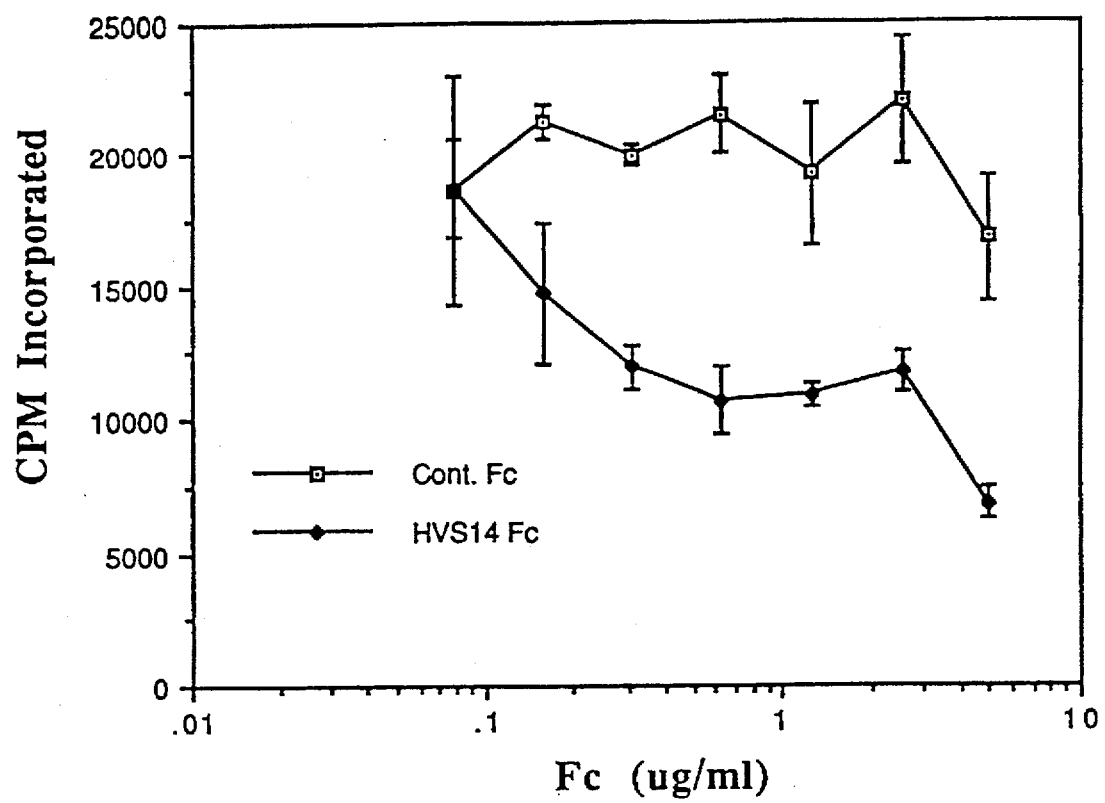
FIG. 4 illustrates the ability of HVS14/Fc to inhibit antigen-specific proliferation of peripheral blood mononuclear cells (PBMCs) induced by PPD. The results demonstrated that HVS14/Fc was able to inhibit a secondary, antigen-specific antibody response.

This example illustrates the ability of HVS14/Fc to inhibit antigen-specific proliferation of peripheral blood mononuclear cells (PBMCs). PBMCs were obtained from the blood of a donor known to be reactive to PPD, by density gradient centrifugation over Histopaque® (Sigma, St. Louis, Mo.). Cell proliferation assays were conducted with PBMCs in RPMI with added 10% heat-inactivated fetal bovine serum (FBS) in the presence of purified PPD (Lederie Laboratories, Pearl River, N.Y.), at 37° C. in a 10% $CO_2$ atmosphere. Approximately $1 \times 10^5$ cells per well were cultured in triplicate in round-bottomed 96-well microtiter plates (Corning) for 7 days, in the presence of HVS14/Fc or a control Fc protein (IL-4/Fc). The cells were pulsed with 1 µCi/well of tritiated thymidine (25 Ci/nmole Amersham, Arlington Heights, Ill.) for the final eight hours of culture. Cells were harvested onto glass fiber discs with an automated cell harvester and incorporated cpm were measured by liquid scintillation spectrometry. Results are shown in FIG. 4. These results demonstrated that HVS14/Fc was able to inhibit a secondary, antigen-specific antibody response.

EXAMPLE 12

Figure 5:
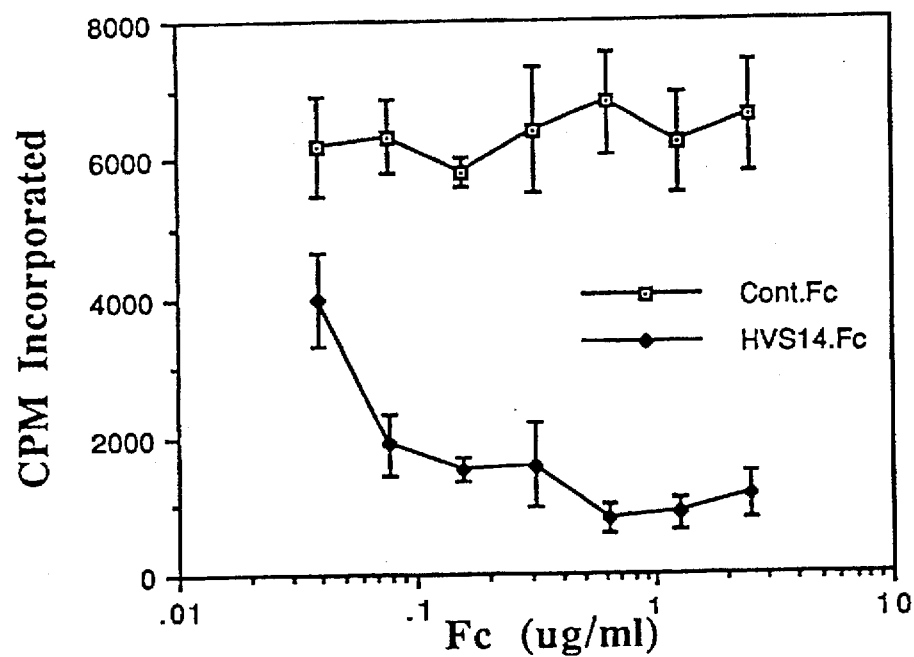
FIG. 5 illustrates the ability of HVS14/Fc to inhibit antigen-specific proliferation of peripheral blood mononuclear cells (PBMCs) induced by tetanus toxoid. The results confirmed that HVS14/Fc was able to inhibit a secondary, antigen-specific antibody response.

This example illustrates the ability of HVS14/Fc to inhibit antigen-specific proliferation of peripheral blood mononuclear cells (PBMCs). PBMCs were obtained from three blood donors known to be reactive against tetanus toxoid, by density gradient centrifugation over Histopaque®(Sigma, St. Louis, Mo.). Cell proliferation assays were conducted with PBMCs in RPMI with added 10% heat-inactivated fetal bovine serum (FBS), in the presence of purified tetanus toxoid (Connaught Laboratory Inc., Swiftwater, Pa.), at 37° C. in a 10% $CO_2$ atmosphere. Approximately $1 \times 10^5$ cells per well were cultured in triplicate in round-bottomed 96-well microtiter plates (Coruing) for 7 days, in the presence of HVS14/Fc or a control Fc protein (7.5/Fc). The cells were pulsed with 1 µCi/well of tritiated thymidine (25 Ci/nmole, Amersham, Arlington Heights, Ill.) for the final eight hours of culture. Cells were harvested onto glass fiber discs with an automated cell harvester and incorporated cpm were measured by liquid scintillation spectrometry. The results, which are shown in FIG. 5, confirmed that HVS14/Fc inhibited a secondary antigen-specific immune response.

EXAMPLE 13

This example describes the expression and processing of full-length HVS14 gene product. The complete coding region of the HVS14 gene was subcloned into an expression vector and transfected into mammalian cells. At 48 hours post DNA transfection, cell culture medium was replaced with methionine-deficient DMEM (Sigma) and cells were starved for 15 minutes at 37° C. Thereafter, 1 ml of methionine deficient medium containing 100 µCi of L-[$^{35}$S] methionine (Amersham, Arlington Heights, Ill.) was added to each petri dish, the culture was incubated at 37° C. for three hours and the supernatants were harvested.

Cell lysates were prepared by dislodging cells into radioimmunoprecipitation buffer (10 mM Tris, [pH 7.4], containing 150 mM NaCl, 1% deoxycholate, 1% Nonidet p-40, and 0.1% SDS, a cocktail of protease inhibitors including 1 mM phenylmethylsulfonyl fluoride, 1 µM pepstatin A, 10 µM leupeptin, 1 mM O-phenanthroline, and 0.02 U/ml aprotinin). The cells were sonically disrupted and sedimented (15,000 rpm for 30 minutes) to remove insoluble macromolecules.

HVS (strain RD) was propagated in owl monkey kidney (OMK) monolayers. The virus infected or mock infected cells were labeled with 300 µCi/ml [$^{35}$S]methionine and cysteine for 16 hours. Supernatants were harvested and precipitated as described below.

For immunoprecipitation, 50 µl of supernatant or cell lysate and 1 µl of polyclonal antiserum or normal mouse serum were added to 200 µl of lysis buffer and incubated at 4° C. for 60 minutes. The antibody-antigen complexes were then incubated with protein A-sepharose beads for an additional hour and washed five times with PBS containing 1% deoxycholate, 1% Nonidet p-40 and 0.1% SDS. The protein A beads were resuspended in Laemmli buffer (Laemmli, U.K., *Nature* 227: 680; 1970) with or without 2-mercaptoethanol. Immunoprecipitates were analyzed on 8–16% polyacrylamide gradient gels containing 0.1% SDS. Gels were prepared for fluorography, dried and exposed to radiographic film (Kodak) for 12 to 72 hours.

The oligosaccharide structure of the HVS14 protein was investigated using N-glycanase, neuraminidase (sialidase), and endo-α-N acetylgalactosaminidase (O-glycanase), substantially as described by Robbins et al. (*Cell* 12: 893, 1977) and Yao et al. (*J. Virol.* 67: 305, 1993). Additional studies were carried out with tunicamycin, which inhibits the addition of N-linked oligosaccharides to glycoproteins. Reagents were purchased from either Sigma or Genzyme (Cambridge, Mass.).

Supernatant from HVS14 transfected cells contained a heterogeneous 50 kd protein that reacted specifically with the HVS14 antiserum. A similar size protein band was present in the HVS infected cell supernatants, but not in the mock-infected OMK cell supernatants. In the transfected cell lysates, the same 50 kd protein band, as well as an additional 38 kd protein was present. Immunoprecipitates electrophoresed under reducing or nonreducing conditions were essentially indistinguishable, suggesting that HVS14 does not dimerize through disulfide bonds.

The apparent difference between the actual and the predicted molecular weight (28 kd) and the heterogeneity of the protein band suggested that this protein was glycosylated. In the presence of tunicamycin, the 50 kd species disappeared, while a protein of approximately 40 kd was detected in the transfected cell supernatants. In the cell lysates, the 50 kd protein shifted to 40 kd, while the 38 kd protein shifted to 28 kd, indicating that both the 50 kd protein and the 38 kd protein contain N-linked carbohydrate moieties. The 28 kd protein likely represents the backbone of the HVS14 protein, which is consistent with the predicted molecular weight.

The N-glycanase digestion results were virtually identical to those obtained with tunicamycin treatment. The presence of a 40 kd protein species in the presence of tunicamycin suggested that the HVS14 backbone (28 kd) was further modified, possibly by O-linked glycosylation. To determine whether HVS14 contained O-linked oligosaccharides, the cell lysates from transfected cells were subjected to serial neuraminidase and O-glycanase digestion. Removal of N-acetylneuraminic acid residues generated a protein with a molecular weight of 42 kd, and subsequent treatment with O-glycanase caused a further shift of HVS14 from 42 kd to 38 kd. These results demonstrate that HVS14 also contains O-linked glycans.

---

We claim:

1. An isolated and substantially homogeneous HVS14 protein capable of binding a Major Histocompatibility Complex Class II molecule, comprising amino acids 34 through 249 of SEQ ID NO:1.

2. An isolated and substantially homogeneous fusion protein comprising HVS14 protein according to claim 1, and an immunoglobulin Fc region.

3. The isolated and substantially homogeneous fusion protein according to claim 2, wherein the immunoglobulin Fc comprises amino acids 1 through 213 of SEQ ID NO:4.

4. The isolated and substantially homogeneous HVS14 protein according to claim 2, wherein the immunoglobulin Fc is a selected from the group consisting of fragments of an immunoglobulin Fc region and Fc muteins.

5. An isolated and substantially homogeneous fusion protein comprising HVS14 protein according to claim 1, and an oligomerizing zipper domain.

6. The isolated and substantially homogeneous HVS14 protein according to claim 5, wherein the zipper domain is selected from the group consisting of amino acids 1 through 33 of SEQ ID NO:6 and amino acids 1 through 33 of SEQ ID NO:7.

7. An isolated and substantially homogeneous HVS14 protein capable of binding a Major Histocompatibility Complex Class II molecule, comprising amino acids 1 through 249 of SEQ ID NO:1.

8. A composition comprising an effective amount of a viral protein according to claim 1, and a suitable diluent or carrier.

9. A composition comprising an effective amount of a viral protein according to claim 2, and a suitable diluent or carrier.

10. A composition comprising an effective amount of a viral protein according to claim 5, and a suitable diluent or carrier.

* * * * *